(12) United States Patent
Kafai et al.

(10) Patent No.: US 10,216,899 B2
(45) Date of Patent: Feb. 26, 2019

(54) SENTENCE CONSTRUCTION FOR DNA CLASSIFICATION

(71) Applicant: Hewlett Packard Enterprise Development LP, Houston, TX (US)

(72) Inventors: Mehran Kafai, Redwood City, CA (US); Kari Lam, Palo Alto, CA (US)

(73) Assignee: HEWLETT PACKARD ENTERPRISE DEVELOPMENT LP, Houston, TX (US)

( * ) Notice: Subject to any disclaimer, the term of this patent is extended or adjusted under 35 U.S.C. 154(b) by 321 days.

(21) Appl. No.: 15/298,412

(22) Filed: Oct. 20, 2016

(65) Prior Publication Data

US 2018/0113978 A1    Apr. 26, 2018

(51) Int. Cl.
G06F 17/30 (2006.01)
G06F 19/28 (2011.01)
G06N 99/00 (2019.01)

(52) U.S. Cl.
CPC ........ *G06F 19/28* (2013.01); *G06F 17/30707* (2013.01); *G06N 99/005* (2013.01)

(58) Field of Classification Search
CPC .................. G06F 17/30707; G06F 19/28
See application file for complete search history.

(56) References Cited

U.S. PATENT DOCUMENTS

| | | | |
|---|---|---|---|
| 5,502,773 A | | 3/1996 | Tibbetts et al. |
| 5,871,697 A | * | 2/1999 | Rothberg ............... C12N 15/10 422/68.1 |
| 8,189,892 B2 | | 5/2012 | Dimirova et al. |
| 8,407,012 B2 | | 3/2013 | Erlich et al. |
| 8,429,216 B2 | | 4/2013 | Eshghi et al. |
| 1,514,235 A1 | | 4/2016 | Eshghi et al. |
| 1,514,279 A1 | | 4/2016 | Kafai et al. |
| 1,516,602 A1 | | 5/2016 | Kafai et al. |
| 1,518,572 A1 | | 6/2016 | Kafai et al. |

(Continued)

OTHER PUBLICATIONS

Ghandi, M. et al., "Enhanced Regulatory Sequence Prediction Using Gapped K-Mer Features." PLoS Comput Biol 10.7 (2014): e1003711.

(Continued)

*Primary Examiner* — Kris E Mackes
(74) *Attorney, Agent, or Firm* — Hewlett Packard Enterprise Patent Department (57) ABSTRACT

In some examples, a method may include obtaining, from a DNA sequence, a DNA bin that includes a number of consecutive DNA elements equal to a bin length parameter and constructing sentences from the DNA bin to form a constructed sentence set that includes a number of sentences equal to a size parameter. Each sentence of the constructed sentence set may be constructed by partitioning the DNA bin into words, each word comprising a number of DNA elements equal to the size parameter. Each sentence of the constructed sentence set may include overlapping DNA elements with other sentences of the constructed sentence set and may start with a different DNA element of the DNA bin. The method may further include using the constructed sentence set to train a classifier and determining a DNA classification for an unclassified DNA subsequence through the classifier trained using the constructed sentence set.

20 Claims, 6 Drawing Sheets

(56) References Cited

U.S. PATENT DOCUMENTS

| | | | | |
|---|---|---|---|---|
| 2002/0174115 | A1* | 11/2002 | shibuya | G06F 19/28 |
| 2003/0143524 | A1 | 7/2003 | Lerner | |
| 2007/0178452 | A1* | 8/2007 | Bouffard | C12N 15/1096 |
| | | | | 435/6.14 |
| 2008/0114564 | A1* | 5/2008 | Ihara | G06F 17/30321 |
| | | | | 702/158 |
| 2013/0332133 | A1* | 12/2013 | Horn | C12N 9/00 |
| | | | | 703/11 |
| 2015/0169824 | A1 | 6/2015 | Kermani et al. | |
| 2016/0103956 | A1* | 4/2016 | Conway | G06F 19/22 |
| | | | | 702/19 |
| 2016/0364522 | A1* | 12/2016 | Frey | G06F 19/22 |
| 2017/0316154 | A1* | 11/2017 | Fitch | G06F 3/0608 |

OTHER PUBLICATIONS

Whitaker, J., et al., "Predicting the Human Epigenome From DNA Motifs." Nature methods 12.3 (2015): 265-272.
Zhou, J. et al., "Predicting Effects of Noncoding Variants With Deep Learning-Based Sequence Model." Nature methods 12.10 (2015), 5 pages.

* cited by examiner

SENTENCE CONSTRUCTION FOR DNA CLASSIFICATION

BACKGROUND

With rapid advances in technology, computing systems are increasingly prevalent in society today. Vast computing systems execute and support applications that communicate and process immense amounts of data. Computing systems may be used to process complex biological datasets, such as identifying and sequencing of deoxyribonucleic acid (DNA) strands and more.

BRIEF DESCRIPTION OF THE DRAWINGS

Certain examples are described in the following detailed description and in reference to the drawings.

DETAILED DESCRIPTION

The discussion herein makes reference to deoxyribonucleic acid (DNA) sequences. A DNA sequence may refer to a representation or ordering of DNA elements, e.g., the base nucleotides of adenine (A), guanine (G), cytosine (C), and thymine (T). One example of DNA sequence is an ordered list of nucleotides in DNA strands, such as DNA strands that form a human genome or human chromosomes. Human gene DNA sequences may include billions of DNA elements, and some animal species have gene DNA sequences with tens of billions DNA elements or more. Processing and classification of DNA sequences can be computationally rigorous and costly.

Examples consistent with the present disclosure may support processing and classification of sequence data sets, such as DNA sequences. As described in greater detail below, DNA sequences may be partitioned into DNA bins of a specified size, and a bin may refer to a subsequence of consecutive elements. Thus, a DNA bin of size 200 may take the form of a string of 200 consecutive DNA elements partitioned from a DNA sequence. As also described in greater detail below, sentences may be constructed from partitioned DNA bins, and a sentence may refer to a collection of words derived from the DNA bin or any other data sequence. A word may refer to a string of sequence elements, such as DNA elements.

Constructed sentence sets with multiple sentences may be formed from DNA bins, and the constructed sentence sets may be used to derive feature vectors. For instance, DNA bins may be embedded as a set of feature vectors of a specified dimension through the constructed sentence sets, and the feature vectors may map functionally similar DNA subsequences to nearby points. The feature vectors may be provided as input samples to machine learning algorithms to train a classifier for DNA classification.

Figure 1:
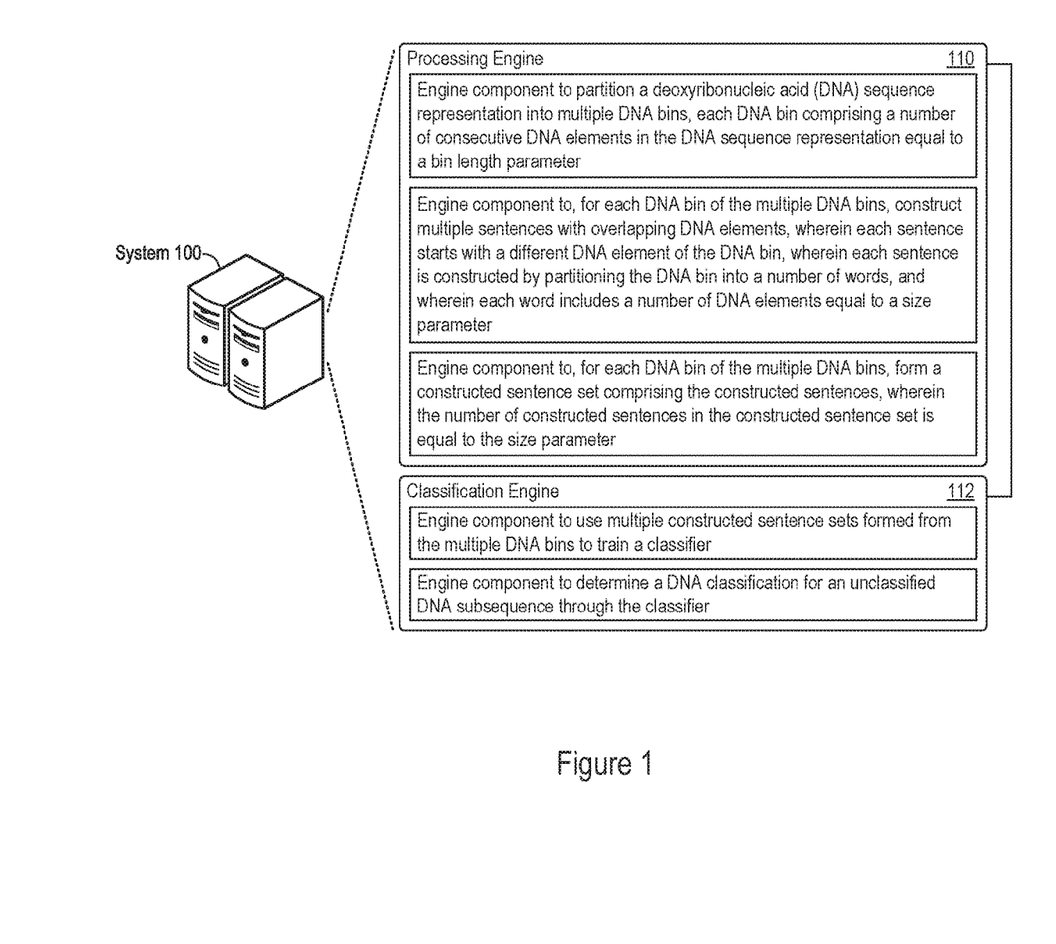
FIG. 1 shows an example of a system that supports sentence construction for DNA classification.

FIG. 1 shows an example of a system 100 that supports sentence construction for DNA classification. The system 100 may take the form of any computing system that includes a single or multiple computing devices such as servers, compute nodes, desktop or laptop computers, smart phones or other mobile devices, tablet devices, embedded controllers, and more.

As described in greater detail herein, the system 100 may partition DNA sequences into DNA bins and process the DNA bins for classifier training. In particular, the system 100 may process a DNA bin to construct multiple sentences that include overlapping DNA elements from the DNA bin. The sentence construction features described herein may support classification of DNA subsequences with increased accuracy and efficiency.

The system 100 may implement various engines to provide or support any of the sentence construction and DNA classification features described herein. In the example shown in FIG. 1, the system 100 implements a processing engine 110 and a classification engine 112. Many of the features disclosed herein are described with respect to the processing engine 110 and the classification engine 112, though various other implementations are possible.

The system 100 may implement the engines 110 and 112 (including components thereof) in various ways, for example as hardware and programming. The programming for the engines 110 and 112 may take the form of processor-executable instructions stored on a non-transitory machine-readable storage medium, and the processor-executable instructions may, upon execution, cause hardware to perform any of the features described herein. In that regard, various programming instructions of the engines 110 and 112 may implement engine components to support or provide the features described herein.

The hardware for the engines 110 and 112 may include a processing resource to execute programming instructions. A processing resource may include various number of processors with a single or multiple processing cores, and a processing resource may be implemented through a single-processor or multi-processor architecture. In some examples, the system 100 implements multiple engines using the same system features or hardware components (e.g., a common processing resource).

The processing engine 110 and the classification engine 112 may include components to process DNA sequences to train a classifier. As shown in the example implementation of FIG. 1, the processing engine 110 may include an engine component to partition a DNA sequence into multiple DNA bins, each DNA bin comprising a number of consecutive DNA elements in the DNA sequence equal to a bin length parameter. The processing engine 110 shown in FIG. 1 may also include an engine component to, for each DNA bin, construct multiple sentences with overlapping DNA elements, wherein each sentence starts with a different DNA element of the DNA bin, wherein each sentence is constructed by partitioning the DNA bin into a number of words, and wherein each word includes a number of DNA elements equal to a size parameter. As yet another example, the processing engine 110 in FIG. 1 may include an engine component to form a constructed sentence set comprising the constructed sentences, wherein the number of constructed sentences in the constructed sentence set is equal to the size parameter.

As also shown in the example implementation in FIG. 1, the classification engine 112 may include engine components to use multiple constructed sentence sets formed from the multiple DNA bins to train a classifier and determine a DNA classification for an unclassified DNA subsequence through the classifier. Consistent with the description above, the engines 110 and 112 may take the form of a processing resource and instructions stored on a non-transitory machine-readable medium. Execution of instructions implementing the engine component features of the engine 110 and 112 may cause the system 100 to perform the implemented features.

Various sentence construction and DNA classification features are described in greater detail next. Many of the examples described below are presented with respect to the processing, sentence construction, and classification of DNA sequences. However, the features described herein may be consistently applied to any sequence data set without natural word boundaries. For instance, the features described herein may be applied to other areas of computational biology, such as prediction of protein structure splice sites (e.g., for editing of ribonucleic acid (RNA) sequences), identification of regulatory elements of DNA strands, and more. Other applications of the features described herein may include processing and classification of social media text, language translations, network data, domain name system (DNS) data, and other data without any or with a limited number of natural word boundaries.

Figure 2:
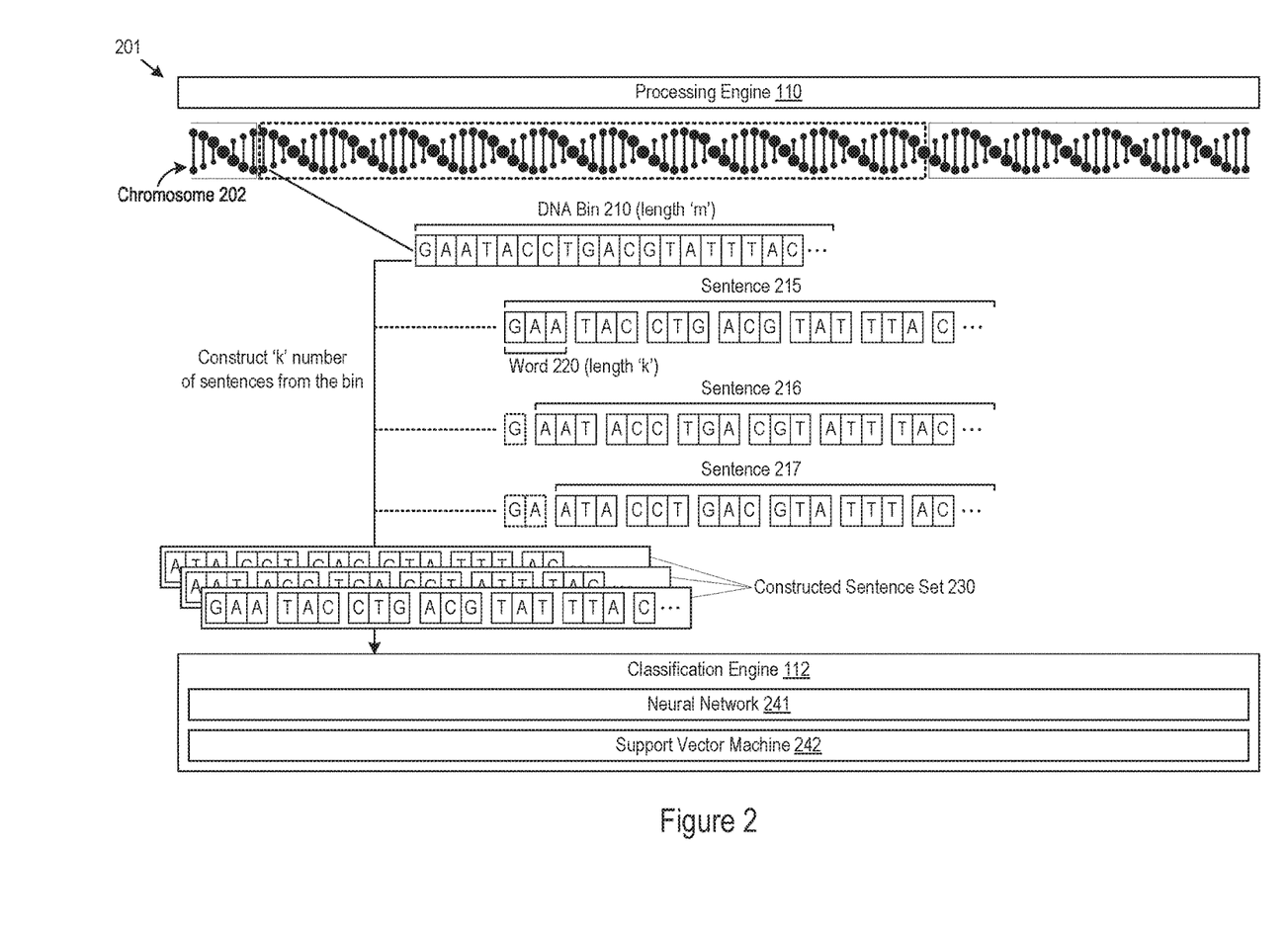
FIG. 2 shows an example of an architecture that supports generation of a constructed sentence set from a DNA bin partitioned from a DNA sequence.

FIG. 2 shows an example of an architecture 201 that supports generation of a constructed sentence set from a DNA bin partitioned from a DNA sequence. The example architecture 201 shown in FIG. 2 includes a processing engine 110 and classification engine 112, which a system may implement in any of the ways described herein.

In operation, the processing engine 110 may partition DNA bins from a DNA sequence. As noted above, a DNA bin may refer to a subsequence of consecutive DNA elements from a DNA sequence. Using a human chromosome as an example DNA sequence, the processing engine 110 may partition a DNA strand of the chromosome into DNA bins. A human chromosome DNA strand may include tens of millions to hundreds of millions of DNA elements, and the processing engine 110 may divide or assign the millions of DNA elements into respective DNA bins. In the example shown in FIG. 2, the processing engine 110 partitions the DNA sequence of a chromosome 202 into multiple DNA bins, including the DNA bin 210 with the subsequence of DNA elements G, A, A, T, A, C, C, T, G, A, C, G, T, A, T, T, T, A, C, . . . .

The processing engine 110 may partition DNA bins to include a specified number of DNA elements, referred to as a bin length or size. The length of partitioned DNA bins may be controlled through a bin length parameter, which is also referenced herein in short form as 'm'. In FIG. 2, the processing engine 110 partitions the DNA bin 210 from a chromosome DNA sequence as a subsequence of length 'm', e.g., with 'm' number of DNA elements. In partitioning DNA bins, the processing engine 110 may do so in a non-overlapping manner such that each DNA element of a partitioned DNA sequence is part of a single DNA bin. Described another way, the processing engine 110 may divide a DNA sequence into DNA bins such that no DNA bin overlaps with any other DNA bin partitioned from the DNA sequence.

To provide an illustrative example, the processing engine 110 may partition a chromosome DNA sequence with 224 million DNA elements (e.g., human chromosome 1). With a bin length parameter configured to a value of 200 (e.g., 'm'=200), the processing engine 110 may partition the initial 200 consecutive DNA elements of the chromosome DNA sequence into a first DNA bin, the next 200 consecutive DNA elements of the chromosome DNA sequence into a second DNA bin, and so on. For a chromosome DNA sequence with more than 224 million DNA elements, the processing engine 110 may partition out at least 1.12 million DNA bins of bin length 200. Responsive to a determination that remaining non-partitioned DNA elements in a DNA sequence are insufficient to partition out another DNA bin (e.g., the remaining non-partitioned DNA elements <200 when 'm'=200), the processing engine 110 may either discard the remaining DNA elements or form an undersized DNA bin with the remaining DNA elements that has a bin length less than the bin length parameter.

From partitioned DNA bins, the processing engine 110 may construct sentences of DNA elements to form constructed sentence sets. In doing so, the processing engine 110 may generate a constructed sentence set for each DNA bin, and the constructed sentence sets may include a number of sentences controlled according to a size parameter. The size parameter may control the number of sentences constructed by the processing engine 110, the size of words in the constructed sentences, or both. The size parameter is also referenced herein in short form as 'k'. In constructing sentences from a DNA bin, the processing engine 110 may, in effect, partition out words from the DNA bin to form sentences. Since a DNA sequence (and thus the DNA bin) does not include natural word boundaries, the processing engine 110 may introduce word boundaries through partitioning of the DNA bin into words, and the size parameter may control the location at which inserted word boundaries occur in a DNA bin.

To illustrate through FIG. 2, the processing engine 110 partitions the DNA bin 210 of length 'm' with a value of 200 according to a size parameter 'k' with a value of 3. As the size parameter has a value of 3 in this example, the processing engine 110 may construct 3 sentences from the DNA bin 210 shown as sentences 215, 216, and 217 in FIG. 2. Each word in the sentences 215, 216, and 217 may include 3 DNA elements according to the size parameter, thus having a word size of 3. Example sentence constructions are described next.

The processing engine 110 may construct the sentence 215 by partitioning the DNA bin 210 into a number of words starting with the initial element of the DNA bin (a nucleotide G in this example). Thus, the processing engine 110 may partition the DNA bin 210 to form DNA elements G,A,A as a first word in the sentence 215 (shown as the word 225). In some examples, the processing engine 110 partitions the DNA bin 210 to form a word by inserting a delimiter, a break, or any other word boundary after the first 3 (or any other 'k' number of) DNA elements of the DNA bin 210. The processing engine 110 may continue to partition subsequent DNA elements in groups of 3 as subsequent words of the sentence 215 until the entirety of the DNA bin 210 is partitioned.

In some examples, the processing engine 110 may discard an end portion of the DNA bin 210 from inclusion in a constructed sentence. The processing engine 110 may do so when, for instance, the remaining non-partitioned DNA elements of the DNA bin 210 do not include enough DNA elements to form another word, e.g., the remaining number of DNA elements is less than the size parameter. In such cases, the processing engine 110 may determine that the remaining DNA elements of the DNA bin 210 do not include enough DNA elements to form another word in the sentence 215, and construct the sentence 215 without the remaining DNA elements.

An example of such a process can be illustrated through the sentence 215 in FIG. 2. In FIG. 2, the sentence 215 starts at the initial element of the DNA bin 210. With the bin length parameter 'm' configured to a value of 200 and the size parameter 'k' configured to a value of 3, the processing engine 110 may partition the first 198 DNA elements of the DNA bin 210 into words of size 3. In doing so, the last 2 DNA elements of the DNA bin 210 may remain. As the remaining 2 DNA elements of the DNA bin 210 do not include enough DNA elements to form a word according to the size parameter ('k'=3), the processing engine 110 may truncate, discard, or otherwise disregard an end portion of the DNA bin 210 to exclude the remaining 2 DNA elements from inclusion in the sentence 215. In this example, the processing engine 110 partitions the DNA bin 210 with bin length 200 into the sentence 215 with 66 words of word size 3, excluding the last 2 DNA elements of the DNA bin 210 from inclusion in the sentence 215.

As noted above, the processing engine 110 may construct multiple sentences from the DNA bin 210. In constructing each of the multiple sentences, the processing engine 110 may partition the entire DNA bin 210, and thus multiple DNA elements of the DNA bin 210 may overlap between the constructed sentences 215, 216, and 217. To vary the multiple constructed sentences, the processing engine 110 may select a different starting DNA element at which partitioning of the DNA bin 210 begins for sentence construction.

To illustrate through FIG. 2, the processing engine 110 selects the initial element of the DNA bin 210 (a nucleotide G) at which to start partitioning of the DNA bin 210 to construct the sentence 215. For the sentence 216, the processing engine 110 may offset the starting DNA element by one, instead determining to initiate the partitioning process from a next consecutive DNA element subsequent to the initial element of the DNA bin 210 (in this example, a nucleotide A that is ordered as the second element in the DNA bin 210). In doing so, the processing engine 110 may construct the sentence 216 without including the initial DNA element of the DNA bin 210 in any words of the sentence 216, in effect discarding the initial DNA element G from inclusion in the sentence 216 (shown as the dotted DNA element next to sentence 216 in FIG. 2). With the starting DNA element for the sentence 216 selected, the processing engine 110 may construct the sentence 216 with words of size 'k' (e.g., 3) by partitioning the DNA bin 210, e.g., in a consistent manner as described above. The processing engine 110 may truncate or discard remaining elements of the DNA bin 210 in constructing sentence 216 as well. Thus, the processing engine 110 may construct the sentence 216 with a different (e.g., offset) starting DNA element from the sentence 215.

In a similar manner, the processing engine 110 may construct the sentence 217 by offsetting the starting DNA element for the sentence 217 past the starting DNA element of the sentence 216. In FIG. 2, the processing engine 110 selects the starting DNA element of the sentence 217 as the third ordered DNA element of the DNA bin 210. In effect, processing engine 110 may discard the initial two DNA elements G and A from inclusion in the sentence 217 (shown as the dotted DNA elements next to sentence 217 in FIG. 2). Then, the processing engine 110 may construct the sentence 217 by partitioning the DNA bin 210 (with the first 2 DNA elements truncated). The processing engine 110 may continue to offset starting DNA elements and construct other sentences until 'k' number of sentences are constructed in accordance with the size parameter.

As described above, the processing engine 110 may generate multiple sentences from a DNA bin 210, and each sentence may be characterized by a different starting DNA element of the DNA bin 210. Described in another way, the processing engine 110 may truncate or discard an initial portion of the DNA bin 210 in generating multiple sentences from a DNA bin 210. For a particular size parameter 'k' and construction of a first sentence, the processing engine 110 may determine not to truncate any initial portion of the DNA bin 210. The processing engine 110 may thus select the initial element of the DNA bin 210 as a starting DNA element for construction of the first sentence. For construction of a second sentence, the processing engine 110 may truncate the initial DNA element of the DNA bin 210, starting at the second-ordered DNA element for starting the second sentence. For construction of a third sentence, the processing engine 110 may truncate the initial two DNA elements of the DNA bin 210, starting the third sentence at a third-ordered DNA element. For construction of a $k^{th}$ sentence for a constructed sentence set, the processing engine 110 may truncate the initial k−1 DNA elements of the DNA bin 210, starting at the $k^{th}$ DNA element for sentence construction.

By constructing multiple sentences from the same DNA bin starting at different and consecutive DNA elements, the processing engine 110 may account for possible starting points of DNA subsequences included in the DNA bin. Without natural word boundaries, the processing engine 110 may account for each possible starting point of a DNA subsequence through consecutively offset starting DNA elements for sentences constructed from a DNA bin. Doing so may increase the accuracy and efficiency at which DNA classification is performed.

Upon constructing 'k' number of sentences from a DNA bin for a particular size parameter, the processing engine 110 may form a constructed sentence set with the 'k' number of constructed sentences. In the example in FIG. 2, the processing engine 110 forms the constructed sentence set 230 that includes the sentences 215, 216, and 217 constructed from the DNA bin 210 according to a size parameter of 3. In some examples, the processing engine 110 forms at least one constructed sentence set for each DNA bin partitioned from a DNA sequence, providing the constructed sentence sets to a classification engine 112. In some examples, the processing engine 110 forms multiple constructed sentence sets for the same DNA bin, an example of which is described in greater detail with reference to FIG. 3.

Turning to classification, the classification engine 112 may use multiple constructed sentence sets formed from DNA bins to train a classifier. The mechanism by which the classification engine 112 does so may vary in any number of ways. In some examples, the classification engine 112 generates feature vectors from the constructed sentence sets and trains a support vector machine (SVM) or other classification model using the feature vectors as input samples. In the example shown in FIG. 2, the classification engine 112 implements a neural network 241 and a SVM 242 for training and classification using constructed sentence sets.

Through a neural network 241, the classification engine 112 may generate feature vectors from constructed sentence sets to represent a distributed representation. Using the constructed sentence set 230 as an example, the classification engine 112 may generate feature vectors for each word in the constructed sentence set 230. In some examples, the neural network 241 employs a continuous bag-of-words model, and the classification engine 112 may provide input words from the sentences 215, 216, and 217 according to a window size parameter used for the continuous bag-of-words model. The neural network 241 may output a feature vector for each of the words, for example at a dimensionality specified through a dimension parameter.

For a particular sentence in a constructed sentence set, the classification engine 112 may combine the feature vectors generated for the words of the particular sentence to obtain a sentence feature vector. Using the sentence 215 as an example, the classification engine 112 may obtain a feature vector generated for each word of the sentence 215 and combine the feature vectors into a sentence feature vector representative of the sentence 215. Example vector combination operations the classification engine 112 may employ include vector addition, multiplication, averaging, and concatenation operations, and the like. As such, the classification engine 112 may generate sentence feature vectors for sentences of received constructed sentence sets. Although one example was presented through a neural network 241 and continuous bag-of-words model, numerous other training models or machine learning processes to generate sentence feature vectors may be additionally or alternatively employed by the classification engine 112.

The classification engine 112 may train a classifier using the generated sentence feature vectors as input samples. In the example shown in FIG. 2, the classification engine 112 uses the SVM 242 to train a classifier. In doing so, the classification engine 112 may obtain baseline labels for the generated sentence feature vectors, e.g., to provide baseline classifications for training the classifier. In some examples, the classification engine 112 trains a binary classifier using obtained positive and negative labels paired to received sentence feature vectors. The labeling may be obtained through comparison of the DNA bins (from which sentences were constructed) to known DNA subsequences.

As an illustrative example, the classification engine 112 may train a binary classifier to classify a specific type of DNA subsequence, such as regulatory elements (also referred to as regulatory sequences). Baseline labels may be applied to DNA bins partitioned from a DNA sequence. For example, a positive label may be assigned to partitioned DNA bins that overlaps with a known regulatory element beyond a percentage threshold whereas a negative label may be assigned to partitioned DNA bins that do not overlap with any known regulatory element beyond the percentage threshold. Positive or negative labels may be assigned to DNA bins partitioned by the processing engine 110, for example through comparison of the partitioned DNA bin with known regulatory elements (or any other selected set of DNA subsequences selected for classification).

When a partitioned DNA bin overlaps with at least one regulatory element by more than the percentage threshold, the classification engine 112 may obtain a positive label for each sentence feature vector generated from sentences constructed from the partitioned DNA bin. Using the DNA bin 210 as an example, the classification engine 112 may obtain a positive label for the three generated sentence feature vectors from sentences 215, 216, and 217 of the constructed sentence set 230 when the DNA bin 210 overlaps one or more known regulatory elements by more than the percentage threshold, and vice versa with regards to a negative label.

The classification engine 112 may also support training of multi-class classifiers. In such examples, the classification engine 112 may obtain particular labels corresponding to the specific regulatory element (or any other class) that the DNA bin 210 overlaps with beyond the percentage threshold, which may include a label indicative that the DNA bin 210 does not overlap with any known regulatory element beyond the percentage threshold. In some examples, the classification engine 112 itself determines the label for sentence feature vectors through comparison of DNA bins to regulatory element DNA subsequences. In other examples, the processing engine 110 or other system logic provides label data to the classification engine 112.

While much of the label description above was described for regulatory elements, any specific type of class of DNA subsequences is contemplated for training and classification by the classification engine 112.

Through the generated sentence feature vectors and corresponding labels, the classification engine 112 may train a classifier. In the example in FIG. 2, the classification engine 112 trains the classifier as a SVM 242, though other classification models are possible as well. To train the classifier, the classification engine 112 may employ various classification training processes such as Concomitant Rank Order (CRO) hashing techniques, e.g., as described in any of U.S. Pat. No. 8,429,216 and U.S. patent application Ser. Nos. 15/142,357; 15/142,798; 15/166,026; and Ser. No. 15/185,727. The classifier trained with the sentence feature vectors and corresponding labels may be employed for classification of regulatory elements in unclassified DNA subsequences, e.g., with either a positive label classify a DNA bin as or including a regulatory element or a negative label indicating otherwise.

The processing engine 110 and classification engine 112 may thus support sentence construction for DNA classification.

Figure 3:
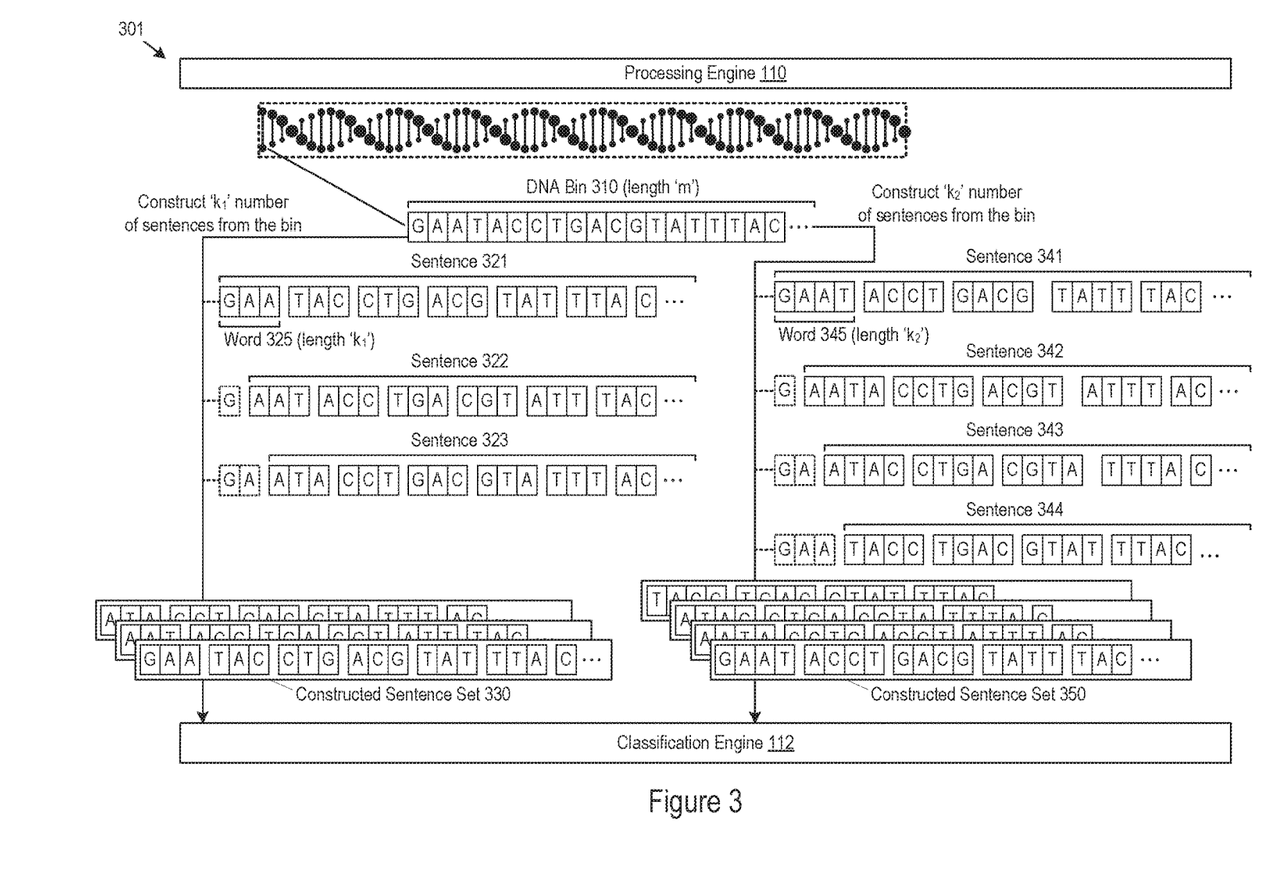
FIG. 3 shows an example of an architecture that supports generation of multiple constructed sentence sets from a DNA bin partitioned from a DNA sequence.

FIG. 3 shows an example of an architecture 301 that supports generation of multiple constructed sentence sets from a DNA bin partitioned from a DNA sequence. The example architecture 301 in FIG. 3 includes a processing engine 110 and a classification engine 112. FIG. 3 illustrates an example by which the processing engine 110 may form multiple constructed sentence sets from the same DNA bin. In the particular example shown in FIG. 3, the processing engine 110 generates two constructed sentence sets from the DNA bin 310 applying a different size parameter for each constructed sentence set.

In forming a first constructed sentence set, the processing engine 110 may employ a first size parameter, shown as '$k_1$' in FIG. 3 with a size parameter value of 3. Thus, in FIG. 3, the processing engine 110 constructs the 3 sentences labeled as 321, 322, and 323 that each include words of size 3 (such as the word 325). The processing engine 110 may construct the sentences 321, 322, and 323 according to any of the various sentence construction features described herein and form the constructed sentence set 330 with the sentences 321, 322, and 323. The processing engine 110 may thus form a first constructed sentence set from the DNA bin 310 according to a first size parameter.

The processing engine 110 may also form a second constructed sentence set from DNA bin 310, and do so according to a second size parameter different from the first size parameter. In the example of FIG. 3, the processing engine 110 employs a second size parameter shown as '$k_2$' with a size parameter value of 4. Accordingly, the processing engine 110 may construct the 4 sentences labeled as 341, 342, 343, and 344 that each include words of size 4 (such as the word 345), doing so through any of the sentence construction features described herein. The processing engine 110 may then form the constructed sentence set 350 with the sentences 341, 342, 343, and 344. In such a way, the processing engine 110 may form multiple constructed sentence sets from the same DNA bin. The processing engine 110 may provide the multiple constructed sentence sets to the classification engine 112 for use in training a classifier.

By forming and providing multiple constructed sentence sets from the same DNA bin, the processing engine 110 may support use of additional and varied sentence feature vectors from the same DNA bin. Doing so may result in increased performance accuracy for a classifier trained by the classification engine 112 using multiple constructed sentence sets formed from same DNA bins. As the increased number of feature vectors (and thus input samples) may cause increased computation requirements, the classification engine 112 may employ CRO hashing techniques to reduce the computational strain and increase efficiency in such examples. Thus, the processing engine 110 may support formation of multiple constructed sentence sets from the same DNA bin using different size parameters.

Figure 4:
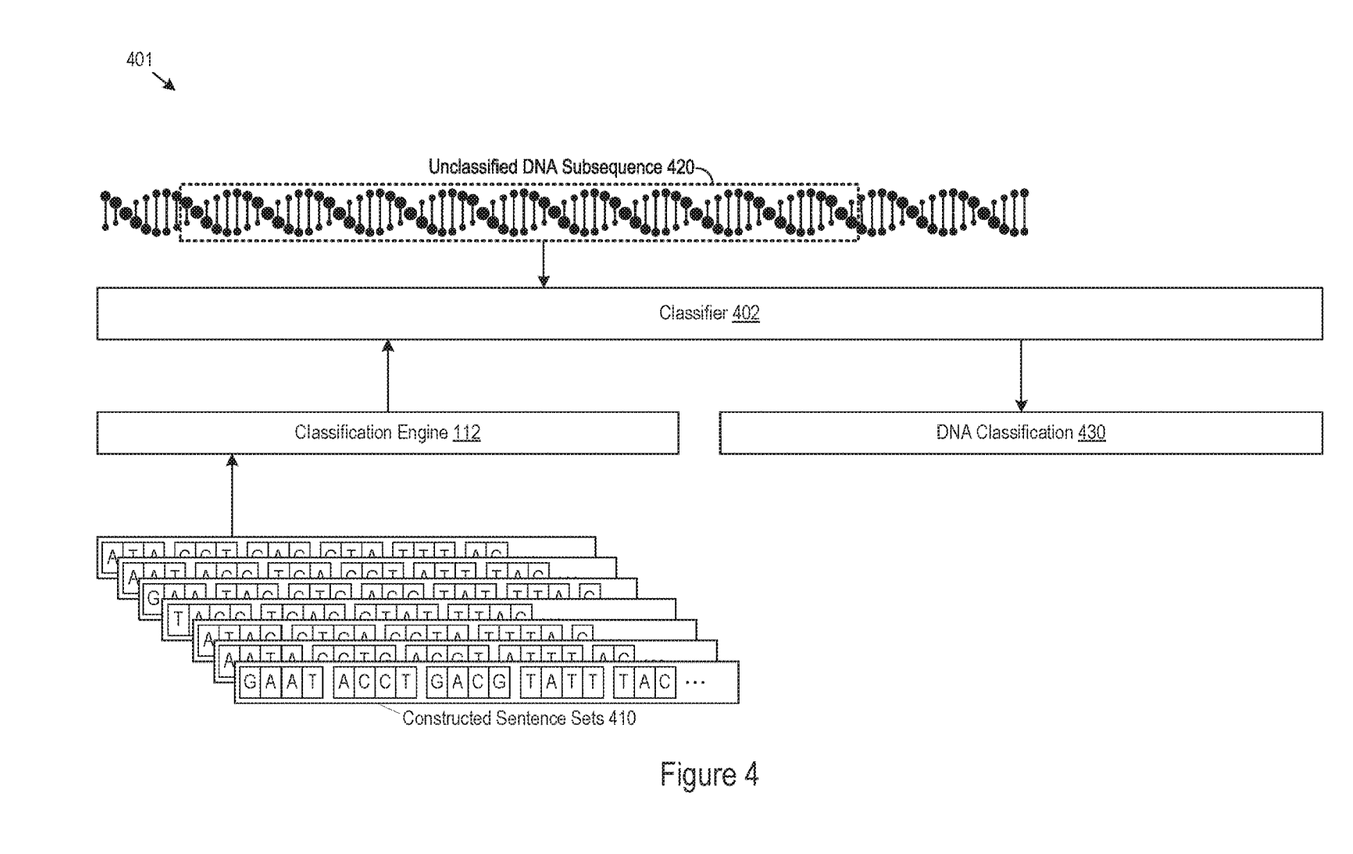
FIG. 4 shows an example of an architecture that supports DNA classification from a classifier trained using constructed sentence sets.

FIG. 4 shows an example of an architecture 401 that supports DNA classification from a classifier trained using constructed sentence sets. In FIG. 4, the architecture 401 includes a classification engine 112 and a classifier 402. Although illustrated separately, the classifier 402 may be implemented as part of the classification engine 112 itself.

In operation, the classification engine 112 may receive constructed sentence sets 410 formed by a processing engine 110. As illustrative numbers for a chromosome DNA sequence with more than 224 million DNA elements, the classification engine 112 may receive at least 1.12 million constructed sentence sets from partitioned DNA bins, and multiple times more when the processing engine 110 forms multiple constructed sentence sets from individual DNA bins. The classification engine 112 may train the classifier 402 using sentence feature vectors generated from the constructed sentence sets 410 in any of the ways described above.

The classifier 402 may classify any number of unclassified DNA subsequences, such as an unclassified DNA subsequence 420 shown in FIG. 4. The unclassified DNA subsequence 420 may be partitioned from a DNA sequence by the classification engine 112, e.g., at a length equal to the bin length parameter. The classifier 402 may output a DNA classification 430 for the unclassified DNA subsequence 420 based on the specific classifier type of the classifier 402 (e.g., binary or multi-class). The DNA classification 430 may take the form a label, e.g., consistent with the labels paired to sentence feature vectors used to train the classifier 402. In this way, the classifier 402 may support classification of DNA subsequences as regulatory elements or any other type of DNA subsequences.

Figure 5:
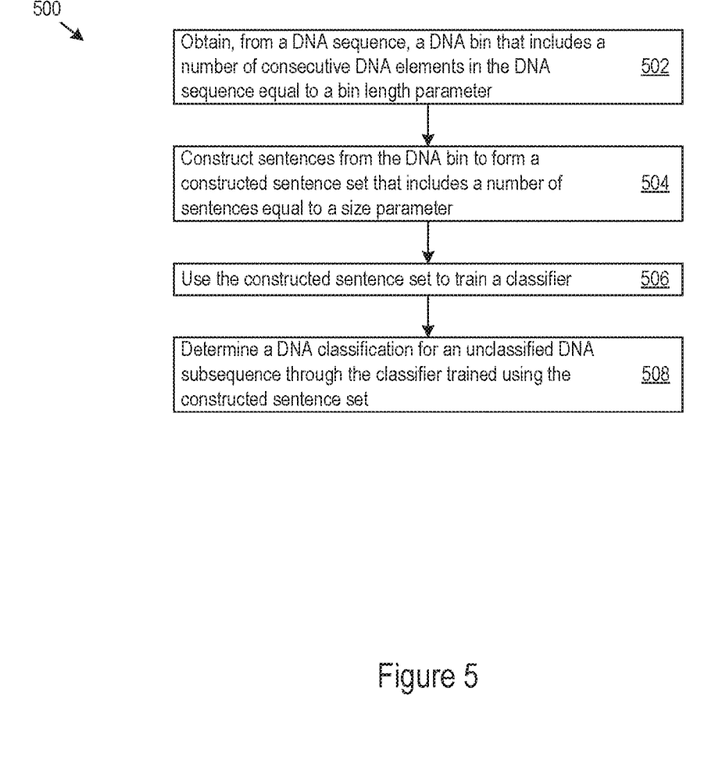
FIG. 5 shows an example of a method that supports sentence construction for DNA classification.

FIG. 5 shows a flow chart of an example method 500 that supports sentence construction for DNA classification. Execution of the method 500 is described with reference to the processing engine 110 and the classification engine 112, though any other device, hardware-programming combination, or other suitable computing system may execute any of the elements of the method 500. As examples, the method 500 may be implemented in the form of executable instructions stored on a machine-readable storage medium or in the form of electronic circuitry.

In implementing, executing, or performing the method 500, a processing engine 110 may obtain, from a DNA sequence, a DNA bin that includes a number of consecutive DNA elements equal to a bin length parameter (502). The processing engine 110 may further construct sentences from the DNA bin to form a constructed sentence set that includes a number of sentences equal to a size parameter (504). Each sentence of the constructed sentence set may be constructed by partitioning the DNA bin into a number of words, and each word may include a number of DNA elements equal to the size parameter. In some examples, each sentence of the constructed sentence set may include overlapping DNA elements with other sentences of the constructed sentence set and may start with a different DNA element of the DNA bin, for example as described above.

In constructing the sentences to form the constructed sentence set, the processing engine 110 may construct a first sentence by partitioning the DNA bin into a number of words starting with a first element of the DNA bin and construct a second sentence by partitioning the DNA bin into a number of words starting with a second element of the DNA bin. The first element at which the first sentence starts may be the initial element of the DNA bin and the second element at which the second sentence starts may be the next DNA element of the DNA bin after the first element. Also, the processing engine 110 may construct the second sentence without including the first element of the DNA bin in any word of the second sentence, which may account for differing possible start position of a DNA subsequence by the first and second sentences. The processing engine 110 may further construct other sentences starting with subsequent elements of the DNA bin respectively until the number of constructed sentences equals the size parameter.

In some examples, the processing engine 110 may determine to exclude a number of DNA elements at the end of the DNA bin from a constructed sentence. The processing engine 110 may do so when, for instance, the remaining DNA elements of the DNA bin do not include enough DNA elements to form another word, e.g., the remaining number of DNA elements is less than the size parameter. Thus, the processing engine 110 may, in constructing a particular sentence, determine that the remaining DNA elements of the DNA bin do not include enough DNA elements to form another word in the particular sentence and construct the particular sentence without the remaining DNA elements. As the starting DNA element varies for different sentences, the number of remaining DNA elements at the end of the DNA bin may likewise vary. In such examples, the processing engine 110 may construct sentences to form the constructed sentence set such that at least two sentences in the constructed sentence set have a different number of words.

The parameters used by the processing engine 110 to partition out DNA bins and form constructed sentence sets may be configurable. For instance, the processing engine 110 may configure the bin length parameter, the size parameter, or both, according to a user input. Other example parameters configurable by the processing engine 110 (or classification engine 112) include distributed neural network parameters such as word window sizes (e.g., for a continuous bag-of-words model), such as vector size parameters for generated feature vectors, SVM parameters, sparsity thresholds used in CRO hashing, and many more.

Turning again to elements of the method 500 shown in FIG. 5, a classification engine 112 may use the constructed sentence set to train a classifier (506). Using the constructed sentence set to train a classifier by the classification engine 112 may include for a particular sentence in the constructed sentence set generating a feature vector for each word in the particular sentence; combining the generated feature vectors to form a sentence feature vector for the particular sentence; and training the classifier as a support vector machine with the sentence feature vector as an input sample. In some examples, the classification engine 112 may further obtain a label for the sentence feature vector based on a percentage of overlap between a DNA bin from which the particular sentence is constructed and a known regulatory element. In such examples, classification engine 112 may train the classifier with the sentence feature vector and the label as the input sample.

The classification engine 112 may intake any number of input samples derived from a DNA sequence (e.g., representing strands of a chromosome), for example sentence feature vectors generated from other DNA bins partitioned from the DNA sequence, other sentence feature vector(s) generated from the same DNA bin according to the same size parameter, or other sentence feature vectors generated from the same DNA bin according to a different size parameter. As noted above, the classification engine 112 may utilize various CRO hashing techniques to translate sentence feature vectors into sparse binary vectors for training a SVM or other classification models.

Turning again to the method 500, the classification engine 112 may determine a DNA classification for an unclassified DNA subsequence through the classifier trained using the constructed sentence set (508). The classifier may utilize a binary DNA classification scheme providing a matching classification output and a non-matching classification output. In some examples, determination of the DNA classification may include classifying the unclassified DNA subsequence as a matching sequence when a threshold percentage of the unclassified DNA subsequence matches a known DNA subsequence (e.g., among a set of regulatory elements). When a threshold percentage of the unclassified DNA subsequence does not match a known DNA subsequence, the classification engine 112 may determine the DNA classification as a non-matching sequence instead.

Although one example was shown in FIG. 5, the elements of the method 500 may be ordered in various ways. Likewise, the method 500 may include any number of additional or alternative elements, including elements implementing any feature described herein with respect to the processing engine 110, the classification engine 112, or a combination thereof. Beyond DNA sequences, the method 500 may be consistently implemented or performed for various other sequence data sets without natural word boundaries, such as RNA sequencing, other sequences in computational biology, numerical data strings, social media data often without natural word boundaries (e.g., hash tags), without punctuation, etc., foreign language translations, network data, DNS data, and more.

Figure 6:
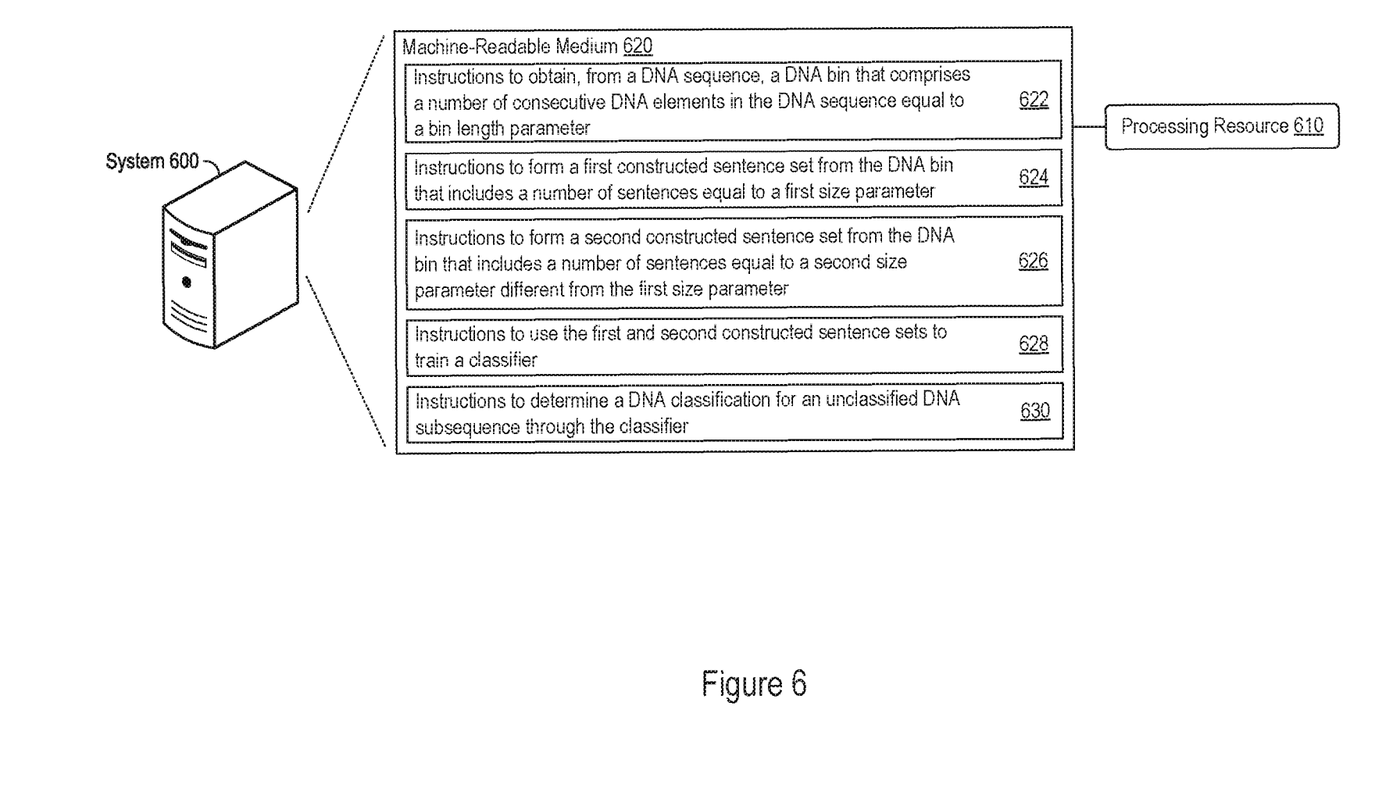
FIG. 6 shows an example of a system that supports sentence construction for DNA classification.

FIG. 6 shows an example of a system 600 that supports sentence construction for DNA classification. The system 600 may include a processing resource 610, which may take the form of a single or multiple processors. The processor(s) may include a central processing unit (CPU), microprocessor, or any hardware device suitable for executing instructions stored on a machine-readable medium, such as the machine-readable medium 620 shown in FIG. 6. The machine-readable medium 620 may be any non-transitory electronic, magnetic, optical, or other physical storage device that stores executable instructions, such as the instructions 622, 624, 626, 628, and 630 shown in FIG. 6. As such, the machine-readable medium 620 may be, for example, Random Access Memory (RAM) such as dynamic RAM (DRAM), flash memory, memristor memory, spin-transfer torque memory, an Electrically-Erasable Programmable Read-Only Memory (EEPROM), a storage drive, an optical disk, and the like.

The system 600 may execute instructions stored on the machine-readable medium 620 through the processing resource 610. Executing the instructions may cause the system 600 to perform any of the features described herein, including according to any features of the processing engine 110, the classification engine 112, or combinations of both.

For example, execution of the instructions 622, 624, 626, 628, and by the processing resource 610 may cause the system 600 to obtain, from a deoxyribonucleic acid (DNA) sequence, a DNA bin that comprises a number of consecutive DNA elements in the DNA sequence equal to a bin length parameter (instructions 622); form a first constructed sentence set from the DNA bin that includes a number of sentences equal to a first size parameter (instructions 624); form a second constructed sentence set from the DNA bin that includes a number of sentences equal to a second size parameter different from the first size parameter (instructions 626); use the first and second constructed sentence sets to train a classifier (instructions 628); and determine a DNA classification for an unclassified DNA subsequence through the classifier (instructions 630).

In formation of the first constructed sentence set through execution of the instructions, each word of the sentences of the first constructed sentence set may have a number of DNA elements equal to the first size parameter, the sentences of the first constructed sentence set may include overlapping DNA elements of the DNA bin, and each sentence of the first constructed sentence set may start at a different DNA element of the DNA bin. Along similar lines, each word of the sentences of the second constructed sentence set may have a number of DNA elements equal to the second size parameter. As such, the first constructed sentence set may include words with different word size from the words of the second constructed set. Sentences of the second constructed sentence set may further include overlapping DNA elements of the DNA bin and each sentence of the second constructed sentence set may start at a different DNA element of the DNA bin.

In some examples, instructions stored on the machine-readable medium 620 may be executable to construct a first sentence in the first constructed sentence set by partitioning the DNA bin into words with a size of the first size parameter starting with the initial element of the DNA bin and construct a first sentence in the second constructed sentence set by partitioning the DNA bin into words with a size of the second size parameter starting also with the initial element of the DNA bin. To use the first and second constructed sentence sets, instructions stored on the machine-readable medium 620 may be executable to train the classifier by generating a first sentence feature vector from a sentence of the first constructed sentence set using a neural network; generating a second sentence feature vector from a sentence of the second constructed sentence set using the neural network; and training the classifier as a support vector machine with the first and second sentence feature vectors as input samples.

The systems, methods, devices, engines, and logic described above, including the processing engine 110 and the classification engine 112, may be implemented in many different ways in many different combinations of hardware, logic, circuitry, and executable instructions stored on a machine-readable medium. For example, the processing engine 110, the classification engine 112, or both, may include circuitry in a controller, a microprocessor, or an application specific integrated circuit (ASIC), or may be implemented with discrete logic or components, or a combination of other types of analog or digital circuitry, combined on a single integrated circuit or distributed among multiple integrated circuits. A product, such as a computer program product, may include a storage medium and machine readable instructions stored on the medium, which when executed in an endpoint, computer system, or other device, cause the device to perform operations according to any of the description above, including according to any features of the processing engine 110, classification engine 112, or both.

The processing capability of the systems, devices, and engines described herein, including the processing engine 110 and the classification engine 112, may be distributed among multiple system components, such as among multiple processors and memories, optionally including multiple distributed processing systems. Parameters, databases, and other data structures may be separately stored and managed, may be incorporated into a single memory or database, may be logically and physically organized in many different ways, and may implemented in many ways, including data structures such as linked lists, hash tables, or implicit storage mechanisms. Programs may be parts (e.g., subroutines) of a single program, separate programs, distributed across several memories and processors, or implemented in many different ways, such as in a library (e.g., a shared library).

While various examples have been described above, many more implementations are possible.

The invention claimed is:

1. A method comprising:
    obtaining, from a deoxyribonucleic acid (DNA) sequence, a DNA bin that comprises a number of consecutive DNA elements in the DNA sequence equal to a bin length parameter;
    constructing sentences from the DNA bin to form a constructed sentence set that includes a number of sentences equal to a size parameter, wherein:
        each sentence of the constructed sentence set includes overlapping DNA elements with other sentences of the constructed sentence set and starts with a different DNA element of the DNA bin; and
        each sentence of the constructed sentence set is constructed by partitioning the DNA bin into a number of words, each word comprising a number of DNA elements equal to the size parameter, and
    using the constructed sentence set to train a classifier; and
    determining a DNA classification for an unclassified DNA subsequence through the classifier trained using the constructed sentence set.

2. The method of claim 1, wherein constructing the sentences to form the constructed sentence set comprises:
    constructing a first sentence by partitioning the DNA bin into a number of words starting with a first element of the DNA bin; and
    constructing a second sentence by partitioning the DNA bin into a number of words starting with a second element of the DNA bin.

3. The method of claim 2, comprising constructing the second sentence without including the first element of the DNA bin in any word of the second sentence.

4. The method of claim 2, wherein:
    the first element at which the first sentence starts is the initial element of the DNA bin; and
    the second element at which the second sentence starts is the next DNA element of the DNA bin after the first element.

5. The method of claim 2, wherein constructing the sentences to form the constructed sentence set further comprises constructing other sentences starting with subsequent elements of the DNA bin respectively until the number of constructed sentences equals the size parameter.

6. The method of claim 1, wherein constructing the sentences from the DNA bin to form the constructed sentence set comprises, in constructing a particular sentence:
    determining that remaining DNA elements of the DNA bin do not include enough DNA elements to form another word in the particular sentence; and
    constructing the particular sentence without the remaining DNA elements.

7. The method of claim 1, comprising constructing the sentences to form the constructed sentence set such that at least two sentences in the constructed sentence set have a different number of words.

8. The method of claim 1, wherein using the constructed sentence set to train a classifier comprises, for a particular sentence in the constructed sentence set:
    generating a feature vector for each word in the particular sentence;
    combining the generated feature vectors to form a sentence feature vector for the particular sentence; and
    training the classifier as a support vector machine with the sentence feature vector as an input sample.

9. The method of claim 8, further comprising obtaining a label for the sentence feature vector based on a percentage of overlap between a DNA bin from which the particular sentence is constructed and a known regulatory element; and
    wherein training comprises training the classifier with the sentence feature vector and the label as the input sample.

10. The method of claim 1, comprising configuring the bin length parameter, the size parameter, or both, according to a user input.

11. A system comprising:
    a processing resource; and
    a non-transitory machine-readable medium comprising instructions that, when executed by the processing resource, cause the system to:
        partition a deoxyribonucleic acid (DNA) sequence into multiple DNA bins, each DNA bin comprising a number of consecutive DNA elements in the DNA sequence equal to a bin length parameter;
        for each DNA bin of the multiple DNA bins:
            construct multiple sentences with overlapping DNA elements, wherein each sentence starts with a different DNA element of the DNA bin, wherein each sentence is constructed by partitioning the DNA bin into a number of words, and wherein each word includes a number of DNA elements equal to a size parameter; and
            form a constructed sentence set comprising the constructed sentences, wherein the number of constructed sentences in the constructed sentence set is equal to the size parameter; and
        use multiple constructed sentence sets formed from the multiple DNA bins to train a classifier; and
        determine a DNA classification for an unclassified DNA subsequence through the classifier.

12. The system of claim 11, wherein the instructions, when executed, cause the system to construct the multiple sentences with overlapping DNA elements by:
    constructing a first sentence by partitioning the DNA bin into a number of words starting with a first element of the DNA bin; and
    constructing a second sentence by partitioning the DNA bin into a number of words starting with a second element of the DNA bin.

13. The non-transitory machine-readable medium of claim 12, wherein the instructions, when executed, cause the system to construct the second sentence without including the first element of the DNA bin in any word of the second sentence.

14. The non-transitory machine-readable medium of claim 12, wherein:
the first element at which the first sentence starts is the initial element of the DNA bin; and
the second element at which the second sentence starts is the next DNA element of the DNA bin after the first element.

15. The non-transitory machine-readable medium of claim 11, wherein the instructions, when executed, cause the system to construct the multiple sentences by, in constructing a particular sentence:
determining that remaining DNA elements of the DNA bin do not include enough DNA elements to form another word in the particular sentence; and
constructing the particular sentence without the remaining DNA elements.

16. The non-transitory machine-readable medium of claim 11, wherein the instructions, when executed, cause the system to construct the multiple sentences with overlapping DNA elements such that at least two sentences of the multiple sentences have a different number of words.

17. A non-transitory machine-readable medium comprising instructions executable by a processing resource to:
obtain, from a deoxyribonucleic acid (DNA) sequence, a DNA bin that comprises a number of consecutive DNA elements in the DNA sequence equal to a bin length parameter;
form a first constructed sentence set from the DNA bin that includes a number of sentences equal to a first size parameter, wherein:
each word of the sentences of the first constructed sentence set has a number of DNA elements equal to the first size parameter;
the sentences of the first constructed sentence set include overlapping DNA elements of the DNA bin; and
each sentence of the first constructed sentence set starts at a different DNA element of the DNA bin; and
form a second constructed sentence set from the DNA bin that includes a number of sentences equal to a second size parameter different from the first size parameter, wherein each word of the sentences of the second constructed sentence set has a number of DNA elements equal to the second size parameter;
use the first and second constructed sentence sets to train a classifier; and
determine a DNA classification for an unclassified DNA subsequence through the classifier.

18. The non-transitory machine-readable medium of claim 17, wherein the sentences of the second constructed sentence set include overlapping DNA elements of the DNA bin and each sentence of the second constructed sentence set starts at a different DNA element of the DNA bin.

19. The non-transitory machine-readable medium of claim 17, wherein the instructions are executable to:
construct a first sentence in the first constructed sentence set by partitioning the DNA bin into words with a size of the first size parameter starting with the initial element of the DNA bin; and
construct a first sentence in the second constructed sentence set by partitioning the DNA bin into words with a size of the second size parameter starting with the initial element of the DNA bin.

20. The non-transitory machine-readable medium of claim 17, wherein the instructions are executable to use the first and second constructed sentence sets to train the classifier by:
generating a first sentence feature vector from a sentence of the first constructed sentence set using a neural network;
generating a second sentence feature vector from a sentence of the second constructed sentence set using the neural network; and
training the classifier as a support vector machine with the first and second sentence feature vectors as input samples.

* * * * *